(12) United States Patent
Steadman et al.

(10) Patent No.: US 7,235,658 B2
(45) Date of Patent: Jun. 26, 2007

(54) IMIDAZOL DERIVATIVES AS RAF KINASE INHIBITORS

(75) Inventors: Jon Graham Steadman, Bishop's Stortford (GB); Andrew Kenneth Takle, Great Dunmow (GB)

(73) Assignee: SmithKline Beecham p.l.c., Brentford, Middlesex (GB)

( * ) Notice: Subject to any disclaimer, the term of this patent is extended or adjusted under 35 U.S.C. 154(b) by 693 days.

(21) Appl. No.: 10/220,674

(22) PCT Filed: Mar. 2, 2001

(86) PCT No.: PCT/GB01/00908

§ 371 (c)(1),
(2), (4) Date: Jan. 7, 2003

(87) PCT Pub. No.: WO01/66539

PCT Pub. Date: Sep. 13, 2001

(65) Prior Publication Data

US 2003/0153588 A1    Aug. 14, 2003

(30) Foreign Application Priority Data

Mar. 6, 2000 (GB) ................... 0005370.2
Mar. 6, 2000 (GB) ................... 0005387.6

(51) Int. Cl.
*C07D 339/02* (2006.01)
(52) U.S. Cl. ...................... 544/242; 546/255
(58) Field of Classification Search ........... 514/275; 544/242; 546/255
See application file for complete search history.

(56) References Cited

U.S. PATENT DOCUMENTS

| | | | |
|---|---|---|---|
| 4,447,431 A * | 5/1984 | Sallmann | 514/256 |
| 5,236,917 A | 8/1993 | Dunlap et al. | |
| 5,514,505 A | 5/1996 | Limburg et al. | |
| 5,717,100 A | 2/1998 | Selnick et al. | |
| 5,859,041 A | 1/1999 | Liverton et al. | |
| 6,548,520 B1 | 4/2003 | Adams et al. | |
| 2003/0134837 A1 | 7/2003 | Gaiba et al. | |
| 2003/0153588 A1 | 8/2003 | Steadman et al. | |
| 2004/0038964 A1 | 2/2004 | Dean et al. | |
| 2004/0053943 A1 | 3/2004 | Adams et al. | |
| 2004/0127496 A1 | 7/2004 | Dean et al. | |
| 2004/0192689 A1 | 9/2004 | Dean et al. | |
| 2004/0198730 A1 | 10/2004 | Dean et al. | |
| 2004/0209883 A1 | 10/2004 | Bamford et al. | |
| 2004/0235843 A1 | 11/2004 | Bamford et al. | |
| 2004/0248896 A1 | 12/2004 | Dean et al. | |
| 2004/0254186 A1 | 12/2004 | Dean et al. | |

FOREIGN PATENT DOCUMENTS

| | | |
|---|---|---|
| GB | 2 306 108 | 4/1994 |
| WO | WO 97/12876 | 4/1997 |
| WO | WO 99/32436 | 4/1997 |
| WO | WO 99/61437 | 12/1999 |
| WO | WO 02/39954 | 5/2002 |

OTHER PUBLICATIONS

D.C. Heimbrock et al., Identification of Potent, Selective Inhibitors of Raf Protein Kinase, Amer. Assoc. for Cancer Res., New Orleans, Apr. 1998.
N.J. Liverton et al., Design and Synthesis of Potent, Selective and Orally Bioavailable Tetrasubstituted Imidazoles of p38 Mitogen Activated Protein Kinase., J. Med. Chem., 1999, 42, 2180-2190.
J. Lisnock et al., Molecular Basis for p38 Protein Kinase Inhibitor Specificity, BioChemistry, 1998, 37, 16573-16581.

(Continued)

*Primary Examiner*—James O. Wilson
*Assistant Examiner*—Jason H. Johnsen
(74) *Attorney, Agent, or Firm*—Grace C. Hsu; Mary E. McCarthy; Charles M. Kinzig

(57) ABSTRACT

Compounds of formula (I):

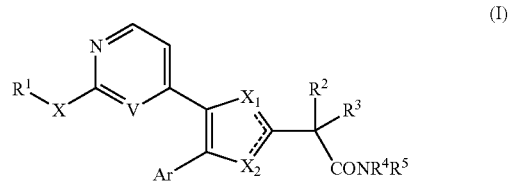

wherein
X is O, $CH_2$, S or NH, or the moiety X—$R^1$ is hydrogen;
V is CH or N;
$R^1$ is hydrogen, $C_{1-6}$alkyl, $C_{3-7}$cycloalkyl, aryl, aryl $C_{1-6}$alkyl, heterocyclyl, heterocyclyl$C_{1-6}$alkyl, heteroaryl, or heteroaryl$C_{1-6}$alkyl any of which except for hydrogen may be optionally substituted;
$R^2$ and $R^3$ independently represent optionally substituted $C_{1-6}$alkyl, or $R^2$ and $R^3$ together with the carbon atom to which they are attached form an optionally substituted $C_{3-7}$cycloalkyl or $C_{3-7}$cycloalkenyl ring; or $R^2$ and $R^3$ together with the carbon atom to which they are attached form an optionally substituted 5 to 7-membered heterocyclyl ring containing up to 3 heteroatoms selected from N, O, S.$R^4$ and $R^5$ independently represent hydrogen, $C_{1-6}$alkyl, $C_{3-7}$cycloalkyl, aryl, aryl $C_{1-6}$alkyl, heteroaryl, heteroaryl$C_{1-6}$alkyl, heterocyclyl, or heterocyclyl$C_{1-6}$alkyl, any of which except for hydrogen may be optionally substituted or $R^4$ and $R^5$ together with the nitrogen atom to which they are attached form 4- to 8-membered ring;
Ar is an aryl or heteroaryl ring either of which may be optionally substituted;
one of $X_1$ and $X_2$ is N and the other is $NR^6$, wherein $R^6$ is hydrogen, $C_{1-6}$alkyl, or aryl$C_{1-6}$alkyl
or pharmaceutically acceptable salts thereof, their use as inhibitors of Raf kinases, and pharmaceutical compositions containing them.

9 Claims, No Drawings

OTHER PUBLICATIONS

L.M. Toledo et al., The Structure-Based Design of ATP-Site Directed Protein Kinase Inhibitors, Current Medicinal Chemistry, 1999, 6, 775-805.

Stover D.R. et al., Recent Advances in protein Kinase inhibition: Current Molecular Scaffolds Used for Inhibitor Synthesis, Current Opinion in Drug Discovery and Development, 1999, 2(4), 274-285.

F.G. Salituro et al., Inhibitors of p38 MAP Kinase: Therapeutic Intervention in Cytokine-Mediated Disease, Current Medicinal Chemistry, 1999, 6, 807-823.

J.L. Adams et al., Recent Progress Towards the Identification of Selective Inhibitors of Serine/Theronine Protein Kinases, Current Opinion in Drug Discovery and Development, 1999, 2(2), 96-109.

Hall-Jackson, C.A. et al., Effect of SB203580 on the Activity of c-Raf in vitro and in vivo Oncogene, (1999) 18, 2047-2054.

J. C. Boehm et al., New Inhibitors of p38 Kinase, Expert Opinion on Therapeutic Patents, (2000), 10, (1).

C. Garcia-Echeverria et al., ATP Site Directed Competitive and Irreversible Inhibtiors of Protein Kinase, Med. Res. Reviews, 2000, 20(1), 28-57.

Wang, Z. et al., Structural Basis of Inhibitor Selectivity in MAP Kinases, Structure, Sep. 15, 1998, 6: 1117-1128.

K. Lackey et al., The Discovery of Potent cRaf1 Kinase Inhibitors, Bioorganic & Medical Chemistry Letters, 10, (2000), 223-226.

J.L. Adams et al., Pyrimidinylimidazole Inhibitors of CSBP/p38 Demonstrating Decreased Inhibition of Hepatic Cytochrome p450 Enzymes, Bioorganic & Medical Chemistry Letters, 8 (1998), 3111-3116.

T.F. Gallagher et al., Regulation of Stress-Induced Cytokine Production by Pyridinylimidazole: Inhibition of CSBP Kinase, Bioorganic & Medical Chemistry, vol. 5, No. 1, 49-64 1997.

J. C. Boehm et al., 1-Substituted 4-Aryl-5-Pyridinylimidazoles: A New Class of Cytokine Suppressive Drugs with Low 5-Lipoxygenase and Cycloxygenase Inhibitory Potency, J. Med. Chem., 1996, 39, 3929-3937.

A. Cuenda et al., SB203580 is a Specific Inhibitor of a MAP Kinase Homologue Which Is Stimulated By Cellular Stresses and Interleukin-1, FEBS Letters, 364, (1995), 229-233.

J. C. Lee et al., p 38 Mitogen-Activated Protein Kinase Inhibitors-Mechanisms and Therapeutic Potentials, Pharmacol. Ther., vol. 82, Nos. 2-3, 389-397, 1999.

Young, P. R. et al., Pyridinyl Imidazole Inhibitors of p38 Mitogen-activated Protein Kinase Bind in the ATP Site, The Journal of Biological Chemistry, vol. 272, No. 18, May 2 Issue, 1997,12116-12121.

J. Dumas et al., Discovery of a New Class of p38 Kinase Inhibitors, Bioorganic & Medical Chemistry Letters, 10, (2000), 2047-2050.

J. Dumas et al., 1-Phenyl-5-pyrazolyl Ureas Potent and Selective p38 Kinase Inhibitors, Bioorganic & Medical Chemistry Letters, 10, (2000), 2051-2054.

L. Revesz et al., SAR of 4-Hydroxypiperidine and Hydroxyalkyl Substituted Heterocycles as Novel p38 Map Kinase Inhibitors, Bioorganic & Medical Chemistry Letters, 10, (2000), 1261-1264.

S.E. deLaszlo et al., Pyrroles and Other Heterocycles as Inhibitors of p38 Kinase, Bioorganic & Medical Chemistry Letters, 8, (1998), 2689-2694.

L. Tong et al., A Highly Specific Inhibitor of Human p38 MAP Kinase Binds in the ATP Pocket, Nature Structural Biology, vol. 4, No. 4, Apr. 1997, 311.

p38 Inhibitors Based on Pyridylurea and Pyridylacetoamide Templates, Expert Opinion on Therapeutic Patents, (2000), 10, (7), 1151-1154.

Two Novel Structural Classes of p38 Kinase Inhibitors, Expert Opinion on Therapeutic Patents, (1999) 9, (4), 477-480.

J. R. Henry et al., Potent Inhibitors of the Map Kinase p38, Bioorganic & Medical Chemistry Letters 8, (1998), 3335-3340.

J. R. Henry et al., p38 Mitogen-Activated Pprotein Kinase as a Target for Drug Discovery, Drugs of the Future, 1999, 24 (12), 1345-1354.

T.B. Lowinger et al., Discovery of a Novel Class of Potent BRAF Kinase Inhibitors: Structure Activity Relationships, 335, Clinical Cancer Research, vol. 6, Nov. 2000, (Supplement) Poster Session, 13, 4533.

D. Eberwein et al., In vivo Activity of a Raf Kinase Inhibitor in Human Tumor Xenograft Models, 406, Clinical Cancer Research, vol. 6, Nov. 2000, (Supplement) Poster Session, 17, 4547.

C.F. Claiborne et al., An Efficient Sythesis of Tertasubstituted Imidazoles from N-(2-Oxo)-Amides, Tetrahedron Letters, 39, (1998), 8939-8942.

M. Antolini et al., Analogues of 4,5-bis(3,5-Dichlorophenyl)-2-Trifluoromethyl-1H-Imidazole as Potential Antibacterial Agents, Bioorganic & Medical Chemistry Letters, 9 (1999), 1023-1028.

M. T. Bilodeau et al., Solid-Supported Synthesis of Imidazoles: A Strategy for Direct Resin-Attachment to the Imidazole Core, J. Org. Chem., 1998, 63, 2800-2801.

P.C. Astles et al., Acyl-CoA:Cholesterol O-Acyltransferase (ACAT) Inhibitors.2.2-(1,3-Dioxan-2-yl)-4,5-Diphenyl-1H-Imidazoles as Potent Inhibitors of ACAT, J. Med.Chem., 1996, 39, 1423.

A. Tannapfel et al., Mutations of the BRAF Gene in Cholangiocarcinoma but not in Hepatoecellular Carcinoma, GUT BMJ Journals, 2003, 52, 706-712.

Y. Cohen et al., BRAF Mutation in Papillary Thyroid Carcinoma, Journal of the National Cancer Institute, vol. 95, No. 8, Apr. 16, 2003.

H. Davies et al., Mutations of the BRAF Gene in Human Cancer, Nature, vol. 417, Jun. 27, 2002, 949-954.

* cited by examiner

IMIDAZOL DERIVATIVES AS RAF KINASE INHIBITORS

This invention relates to novel compounds and their use as pharmaceuticals particularly as Raf kinase inhibitors for the treatment of neurotraumatic diseases.

Raf protein kinases are key components of signal transduction pathways by which specific extracellular stimuli elicit precise cellular responses in mammalian cells. Activated cell surface receptors activate ras/rap proteins at the inner aspect of the plasmamembrane which in turn recruit and activate Raf proteins. Activated Raf proteins phosphorylate and activate the intracellular protein kinases MEK1 and MEK2. In turn, activated MEKs catalyse phosphorylation and activation of p42/p44 mitogen-activated protein kinase (MAPK). A variety of cytoplasmic and nuclear substrates of activated MAPK are known which directly or indirectly contribute to the cellular response to environmental change. Three distinct genes have been identified in mammals that encode Raf proteins; A-Raf, B-Raf and C-Raf (also known as Raf-1) and isoformic variants that result from differential splicing of MRNA are known.

Inhibitors of Raf kinases have been suggested for use in disruption of tumor cell growth and hence in the treatment of cancers, e.g. histiocytic lymphoma, lung adenocarcinoma, small cell lung cancer and pancreatic and breast carcinoma; and also in the treatment and/or prophylaxis of disorders associated with neuronal degeneration resulting from ischemic events, including cerebral ischemia after cardiac arrest, stroke and multi-infarct dementia and also after cerebral ischemic events such as those resulting from head injury, surgery and/or during childbirth.

We have now found a group of novel compounds that are inhibitors of Raf lcinases, in particular inhibitors of B-Raf kinase.

According to the invention there is provided compounds of formula (I):

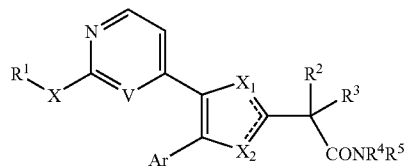

(I)

wherein
X is O, CH$_2$, S or NH, or the moiety X—R$^1$ is hydrogen;
V is CH or N;
R$^1$ is hydrogen, C$_{1-6}$alkyl, C$_{3-7}$cycloalkyl, aryl, aryl C$_{1-6}$alkyl, heterocyclyl, heterocyclylC$_{1-6}$alkyl, heteroaryl, or heteroarylC$_{1-6}$alkyl any of which, except for hydrogen, may be optionally substituted;
R$^2$ and R$^3$ independently represent optionally substituted C$_{1-6}$alkyl, or R$^2$ and R$^3$ together with the carbon atom to which they are attached form an optionally substituted C$_{3-7}$cycloalkyl or C$_{3-7}$cycloalkenyl ring; or R$^2$ and R$^3$ together with the carbon atom to which they are attached form an optionally substituted 5 to 7-membered heterocyclyl ring containing up to 3 heteroatoms selected from N, O, S.
R$^4$ and R$^5$ independently represent hydrogen, C$_{1-6}$alkyl, C$_{3-7}$cycloalkyl, aryl, arylC$_{1-6}$alkyl, heteroaryl, heteroaryl C$_{1-6}$alkyl, heterocyclyl, or heterocyclylC$_{1-6}$alkyl, any of which, except for hydrogen, may be optionally substituted or R$^4$ and R$^5$ together with the nitrogen atom to which they are attached form 4- to 8-membered ring;
Ar is an aryl or heteroaryl ring either of which may be optionally substituted;
one of X$_1$ and X$_2$ is N and the other is NR$^6$, wherein R$^6$ is hydrogen, C$_{1-6}$alkyl, or arylC$_{1-6}$alkyl;
or pharmaceutically acceptable salts thereof.

As used herein, the double bond indicated by the dotted lines of formula (I), represent the possible tautomeric ring forms of the compounds falling within the scope of this invention, the double bond being to the unsubstituted nitrogen atom.

Alkyl and alkenyl groups referred to herein, individually or as part of larger groups e.g. alkoxy, may be straight or branched groups containing up to six carbon atoms and are optionally substituted by one or more groups selected from the group consisting of aryl, heteroaryl, heterocyclyl, C$_{1-6}$alkoxy, C$_{1-6}$alkylthio, arylC$_{1-6}$alkoxy, arylC$_{1-6}$alkylthio, amino, mono- or di-C$_{1-6}$alkylamino, cycloalkyl, cycloalkenyl, carboxy and esters thereof, amide, sulphonamido, ureido, guanidino, C$_{1-6}$alkylguanidino, amidino, C$_{1-6}$alkylamidino, C$_{1-6}$acyloxy, azido, hydroxy, hydroxyimino and halogen. Preferably the optional substituent contains a solubilising group; suitable solubilising moieties will be apparent to those skilled in the art and include hydroxy and amine groups. Even more preferably the optional substituent include heterocyclyl, amino, mono- or di-C$_{1-6}$alkylamino, amide, and hydroxy or any combination thereof.

Cycloalkyl and cycloalkenyl groups referred to herein include groups having from three to seven ring carbon atoms and are optionally substituted as described hereinabove for alkyl and alkenyl groups.

When used herein, the term "aryl" includes, unless otherwise defined, single and fused rings suitably containing from 4 to 7, preferably 5 or 6, ring atoms in each ring, which rings, may each be unsubstituted or substituted by, for example, up to three substituents.

Suitable aryl groups include phenyl and naphthyl such as 1-naphthyl or 2-naphthyl.

When used herein the term "heterocyclyl" includes, unless otherwise defined, non-aromatic, single and fused, rings suitably containing up to four heteroatoms in each ring, each of which is selected from O, N and S, which rings, may be unsubstituted or substituted by, for example, up to three substituents. Each heterocyclic ring suitably has from 4 to 7, preferably 5 or 6, ring atoms. A fused heterocyclic ring system may include carbocyclic rings and need include only one heterocyclic ring. Examples of heterocyclyl groups include pyrrolidine, piperidine, piperazine, morpholine, imidazolidine and pyrazolidine.

When used herein, the term "heteroaryl" includes, unless otherwise defined, mono- and bicyclic heteroaromatic ring systems comprising up to four, preferably 1 or 2, heteroatoms each selected from O, N and S. Each ring may have from 4 to 7, preferably 5 or 6, ring atoms. A bicyclic heteroaromatic ring system may include a carbocyclic ring. Examples of heteroaryl groups include pyrrole, quinoline, isoquinoline, pyridine, pyrimidine, oxazole, thiazole, thiadiazole, triazole, imidazole and benzimidazole.

Aryl, hererocyclyl and heteroaryl groups may be optionally substituted by preferably up to three substituents. Suitable substituents include halogen, C$_{1-6}$alkyl, aryl, aryl C$_{1-6}$alkyl, C$_{1-6}$alkoxy, C$_{1-6}$alkoxy C$_{1-6}$alkyl, halo C$_{1-6}$alkyl, arylC$_{1-6}$alkoxy, hydroxy, nitro, cyano, azido, amino, mono- and di-N-C$_{1-6}$alkylamino, acylamino, arylcarbonylamino, acyloxy, carboxy, carboxy salts, carboxy esters, carbamoyl, mono- and di-N-C$_{1-6}$alkylcarbamoyl, C$_{1-6}$-alkoxycarbonyl, aryloxycarbonyl, ureido, guanidino, C$_{1-6}$alkylguanidino, amidino, C$_{1-6}$alkylamidino, sulphonylamino, aminosulphonyl, C$_{1-6}$alkylthio, C$_{1-6}$alkylsulphinyl, C$_{1-6}$alkylsulphonyl, heterocyclyl, heteroaryl, heterocyclyl C$_{1-6}$alkyl, hydroxyimino-C$_{1-6}$alkyl and heteroaryl C$_{1-6}$alkyl. Preferably the optional substituent contains a solubilising group; suitable solubilising moieties will be apparent to those skilled in the art and include hydroxy and amine groups. Even more preferably the optional substituent include heterocyclyl, amino, mono- or di-C$_{1-6}$alkylamino, amide, and hydroxy or any combination thereof.

X is preferably NH or X—R$^1$ is hydrogen and when X is NH, R$^1$ is preferably C$_{1-6}$alkyl or hydrogen.

When V is CH, X—R$^1$ is preferably hydrogen.

When V is N, X—R$^1$ is preferably NH$_2$.

Most preferably X—R$^1$ is hydrogen.

Ar is preferably an optionally substituted phenyl.

Preferred substituents for the group Ar include halo, hydroxy, hydroxy C$_{1-6}$alkyl, e.g. hydroxymethyl, hydroxyimino-C$_{1-6}$alkyl and C$_{1-6}$alkoxy e.g. methoxy, more preferred are halo and hydroxy. When Ar is phenyl the substituents are preferably present in the 3-position or the 3,4-positions. When Ar is phenyl it preferably has a 3-hydroxy substituent. Particular substitution patterns for Ar when phenyl are 3-hydroxy, 3-hydroxy-4-halo e.g. 3-hydroxy-4-chloro or 3-hydroxy-4-bromo, 3-hydroxy-4-methyl and 3-hydroxy-4-methoxy, more particularly 3-hydroxy-4-chloro.

R$^2$ and R$^3$ independently represent C$_{1-6}$alkyl or R$^2$ and R$^3$ together with the carbon atom to which they are attached form an optionally substituted C$_{3-7}$cycloalkyl or C$_{3-7}$cycloalkyl ring. Alternatively R$^2$ and R$^3$ together with the carbon atom to which they are attached form an optionally substituted 5 to 7-membered heterocyclyl ring containing up to 3 heteroatoms selected from N, O and S.

R$^2$ and R$^3$ preferably independently represent optionally substituted C$_{1-6}$alkyl, or R$^2$ and R$^3$ together with the carbon atom to which they are attached form an optionally substituted C$_{3-7}$cycloalkyl or C$_{5-7}$cycloalkenyl ring. More preferably R$^2$ and R$^3$ represent C$_{1-6}$alkyl, or R$^2$ and R$^3$ together with the carbon atom to which they are attached form an optionally substituted C$_{3-7}$cycloalkyl ring. In particular R$^2$ and R$^3$ represent methyl Preferably R$^4$ and R$^5$ are independently hydrogen, C$_{1-6}$alkyl, arylC$_{1-6}$alkyl, C$_{3-7}$cycloalkyl any of which except hydrogen may be optionally substituted or R$^4$ and R$^5$ together with the nitrogen to which they are attached from an optionally substituted 5 or 6 membered ring optionally containing up to 2 heteroatoms selected from N or O, for example morpholine, pyrrolidine or piperazine.

The compounds of formula (I) preferably have a molecular weight of less than 800.

Particular compounds according to the invention include those mentioned in the examples and their pharmaceutically acceptable salts. It will be understood that the invention includes pharmaceutically acceptable derivatives of compounds of formula (I) and that these are included within the scope of the invention.

As used herein "pharmaceutically acceptable derivative" includes any pharmaceutically acceptable salt, ester or salt of such ester of a compound of formula (I) which, upon administration to the recipient, is capable of providing (directly or indirectly) a compound of formula (I) or an active metabolite or residue thereof.

It will be appreciated that for use in medicine the salts of the compounds of formula (I) should be pharmaceutically acceptable. Suitable pharmaceutically acceptable salts will be apparent to those skilled in the art and include those described in J. Pharm. Sci., 1977, 66, 1-19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. Other salts e.g. oxalates, may be used, for example in the isolation of compounds of formula (I) and are included within the scope of this invention.

The compounds of this invention may be in crystalline or non-crystalline form, and, if crystalline, may optionally be hydrated or solvated. This invention includes within its scope stoichiometric hydrates as well as compounds containing variable amounts of water.

The invention extends to all isomeric forms including stereoisomers and geometric isomers of the compounds of formula (I) including enantiomers and mixtures thereof e.g. racemates. The different isomeric forms may be separated or resolved one from the other by conventional methods, or any given isomer may be obtained by conventional synthetic methods or by stereospecific or asymmetric syntheses.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure.(% are on a weight for weight basis). Impure preparations of the compounds may be used for preparing the more pure forms used in the pharmaceutical compositions.

Compounds of formula (I) are imidazole derivatives which may be readily prepared using procedures well-known to those skilled in the art, and described in, for instance, Comprehensive Heterocyclic Chemistry, Editors Katritzky and Rees, Pergamon Press, 1984, 5, 457-497, from starting materials which are either commercially available or can be prepared from such by analogy with well-known processes. A key step in many such syntheses is the formation of the central imidazole nucleus. Suitable procedures are described in inter alia U.S. Pat. No's. 3,707,475 and 3,940,486 which are herein incorporated by reference in their entirety. These patents describe the synthesis of α-diketones and α-hydroxyketones (benzoins) and their subsequent use in preparing imidazoles and N-hydroxyl imidazoles.

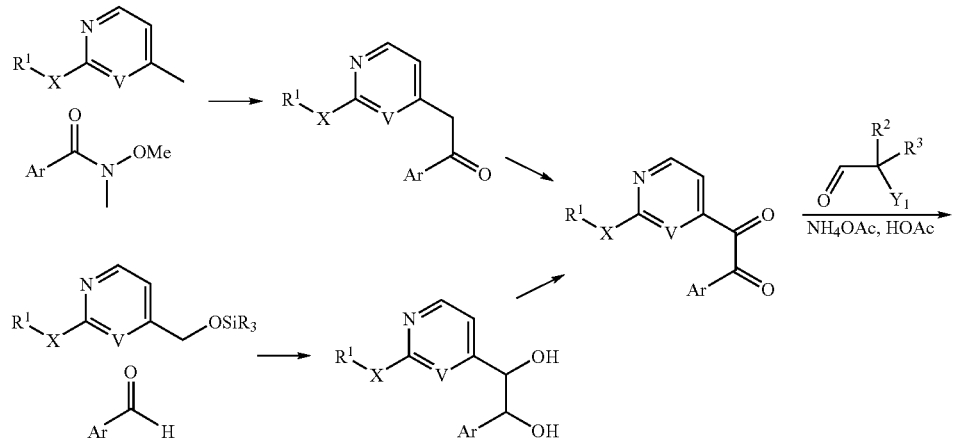

-continued

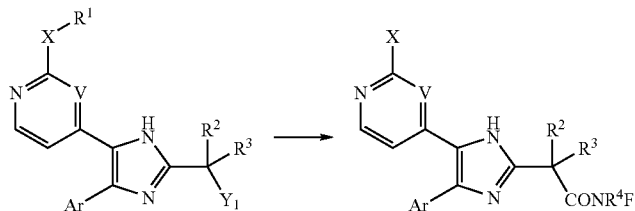

Preferred methods for preparing compounds of this invention are as outlined in the above scheme, wherein $Y_1$ is COOH or a $C_{1-6}$ alkyl or $arylC_{1-6}$alkyl ester thereof. α-Diketones are prepared by condensation of the anion of, for example, a 4-substituted pyridine derivative (V=CH, $R^1$—X=H) with the Weinreb amide of an aryl acid or an aryl-aldehyde, followed by oxidation of the intermediate product. Heating the diketone with an aldehyde and ammonium acetate in acetic acid allows access to the imidazole nucleus. Thereafter, the group $Y_1$ may be converted into a group Y using conventional functional group interconversion procedures. Functional group transformations are well known in the art and are described in, for instance, *Comprehensive Organic Functional Group Transformations*, eds. A. R. Katritzky, O. Meth-Cohn, and C. W. Rees (Elsevier Science Ltd., Oxford, 1995), *Comprehensive Organic Chemistry*, eds. D. Barton and W. D. Ollis (Pergamon Press, Oxford, 1979), and *Comprehensive Organic Transformations*, R. C. Larock (VCH Publishers Inc., New York, 1989). The group $Y_1$ is preferably $COOCH_3$.

Non-selective alkylation of the imidazole nitrogen (using one of the procedures outlined in N. J. Liverton et at; *J. Med. Chem.*, 1999, 42, 2180-2190) with a compound of formula $L-R^6$ wherein L is a leaving group, e.g. halo, sulfonate or triflate, will yield both isomers of the compounds of formula (I) where $X_1$ or $X_2$ is $NR^6$ in which $R^6$ is other than hydrogen, the isomers can be separated by chromatographic methods.

During the synthesis of the compounds of formula (I) labile functional groups in the intermediate compounds, e.g. hydroxy, carboxy and amino groups, may be protected. A comprehensive discussion of the ways in which various labile functional groups may be protected and methods for cleaving the resulting protected derivatives is given in for example *Protective Groups in Organic Chemistry*, T. W. Greene and P. G. M. Wuts, (Wiley-Interscience, New York, 2nd edition, 1991).

The compounds of formula (I) may be prepared singly or as compound libraries comprising at least 2, for example 5 to 1,000 compounds, and more preferably 10 to 100 compounds of formula (I). Libraries of compounds of formula (I) may be prepared by a combinatorial 'split and mix' approach or by multiple parallel synthesis using either solution phase or solid phase chemistry, by procedures known to those skilled in the art.

Thus according to a further aspect of the invention there is provided a compound library comprising at least 2 compounds of formula (I), or pharmaceutically acceptable salts thereof.

Pharmaceutically acceptable salts may be prepared conventionally by reaction with the appropriate acid or acid derivative.

The novel carboxylic esters and the corresponding acids of formula (II) which are used as intermediates in the synthesis of the compounds of formula (I) also form part of the present invention:

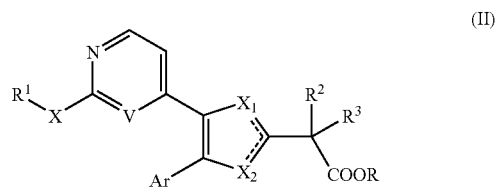

wherein X, V, $R^1$, $R^2$, $R^3$, Ar, $X_1$ and $X_2$ are as defined for formula (I) and R is hydrogen, $C_{1-6}$alkyl or $arylC_{1-6}$alkyl.

As indicated above the compounds of formula (I) and their pharmaceutically acceptable salts are useful for the treatment and/or prophylaxis of disorders in which Raf kinases, in particular B-Raf kinase, are implicated.

According to a further aspect of the invention there is provided the use of a compound of formula (I) or a pharmaceutically acceptable salt thereof as an inhibitor of B-Raf kinase.

As indicated above the compounds of formula (I) and their pharmaceutically acceptable salts are useful the treatment and/or prophylaxis of disorders associated with neuronal degeneration resulting from ischemic events.

According to a further aspect of the invention there is provided a method of treatment or prophylaxis of a neurotraumatic disease, in a mammal in need thereof, which comprises administering to said mammal an effective amount of a compound of formula (I) or a pharmaceutically acceptable salt thereof.

According to a further aspect of the invention there is provided the use of a compound of formula (I) or a pharmaceutically acceptable salt thereof in the manufacture of a medicament for the prophylactic or therapeutic treatment of any disease state in a human, or other mammal, which is exacerbated or caused by a neurotraumatic event.

Neurotraumatic diseases/events as defined herein include both open or penetrating head trauma, such as caused by surgery, or a closed head trauma injury, such as caused by an injury to the head region. Also included within this definition is ischemic stroke, particularly to the brain area, transient ischemic attacks following coronary by-pass and cognitive decline following other transient ischemic conditions.

Ischemic stroke may be defined as a focal neurologic disorder that results from insufficient blood supply to a particular brain area, usually as a consequence of an embolus, thrombi, or local atheromatous closure of the blood vessel. Roles for stress stimuli (such as anoxia), redox injury, excessive neuronal excitatory stimulation and inflammatory cytokines in this area has been emerging and the present invention provides a means for the potential treatment of these injuries. Relatively little treatment, for an acute injury such as these has been available.

The compounds of the invention may also be used in the treatment or prophylaxis of cancers.

The compounds of the invention may also be of use for the treatment or prophylaxis of CSBP/p38 mediated diseases as described in WO 99/01131 and WO 99/01130.

It will be appreciated by those skilled in the art that reference herein to treatment extends to prophylaxis as well as the treatment of established infections or symptoms.

In order to use the compounds of formula (I) in therapy, they will normally be formulated into a pharmaceutical composition in accordance with standard pharmaceutical practice.

According to a further aspect of the invention there is provided a pharmaceutical composition comprising a compound of formula (I) or a pharmaceutically acceptable salt thereof and a pharmaceutically acceptable carrier.

The compounds of formula (I) may conveniently be administered by any of the routes conventionally used for drug administration, for instance, parenterally, orally, topically or by inhalation. The compounds of formula (I) may be administered in conventional dosage forms prepared by combining it with standard pharmaceutical carriers according to conventional procedures. The compounds of formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable carrier is dictated by the amount of compound of formula (I) with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 g. When a liquid carrier is used, the preparation will be in the form of a syrup, emulsion, soft gelatin capsule, sterile injectable liquid such as an ampoule or nonaqueous liquid suspension.

The compounds of formula (I) are preferably administered parenterally, that is by intravenous, intramuscular, subcutaneous intranasal, intrarectal, intravaginal or intraperitoneal administration. The intravenous form of parenteral administration is generally preferred. The compounds may be administered as a bolus or continuous infusion e.g. over 3 days. Appropriate dosage forms for such administration may be prepared by conventional techniques.

The compounds of formula (I) may also be administered orally. Appropriate dosage forms for such administration may be prepared by conventional techniques.

The compounds of formula (I) may also be administered by inhalation, that is by intranasal and oral inhalation administration. Appropriate dosage forms for such administration, such as aerosol formulations, may be prepared by conventional techniques.

The compounds of formula (I) may also be administered topically, that is by non-systemic administration. This includes the application of the inhibitors externally to the epidermis or the buccal cavity and the instillation of such a compound into the ear, eye and nose, such that the compound does not significantly enter the blood stream.

For all methods of use disclosed herein the daily oral dosage regimen will preferably be from about 0.1 to about 80 mg/kg of total body weight, preferably from about 0.2 to 30 mg/kg, more preferably from about 0.5 mg to 15 mg. The daily parenteral dosage regimen about 0.1 to about 80 mg/kg of total body weight, preferably from about 0.2 to about 30 mg/kg, and more preferably from about 0.5 mg to 15 mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of the inhibitors will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of the inhibitors given per day for a defined number of days, can be ascertained by those skilled in the art using conventional course of treatment determination tests. In the case of pharmaceutically acceptable salts the above figures are calculated as the parent compound of formula (I).

No toxicological effects are indicated/expected when a compound of formula (I) is administered in the above mentioned dosage range.

All publications, including but not limited to patents and patent applications, cited in this specification are herein incorporated by reference as if each individual publication were specifically and individually indicated to be incorporated by reference herein as though fully set forth.

The following Examples illustrate the preparation of pharmacologically active compounds of the invention and the following Descriptions illustrate the preparation of intermediates used in the preparation of these compounds.

Abbreviations used herein are as follows—THF means tetrahydrofuran.

Description 1: 2-[4-(4-Chloro-3-methoxyphenyl)-5-pyridin-4-yl-1H-imidazol-2-yl]-2-methyl propionic acid methyl ester Step 1. 4-Chloro-3,N-dimethoxy-N-methyl-benzamide A suspension of 4-chloro-3-methoxybenzoic acid (F. Claudi et al *J. Med. Chem.*, 1992, 35, 4408) (37.2 g, 0.2 mol) in dichloromethane (500 ml) containing oxalyl chloride (26 ml) was treated with N,N-dimethylformamide (10 drops). After stirring at room temperature for 6 hours the solution was concentrated at reduced pressure, additional dichloromethane was added to the residue and the solvent was re-evaporated. The residue was dissolved in acetonitrile (600 ml) and methoxymethylamine hydrochloride (20.5 g, 0.21 mol) added. The mixture was cooled in an ice-bath, a solution of pyridine (80 ml) in acetonitrile (150 ml) added dropwise, and the mixture stirred at room temperature for 18 hours. The solution was concentrated and the residue partitioned between ethyl acetate and saturated potassium carbonate solution. The organic layer was separated, washed with brine, dried ($MgSO_4$) and concentrated at reduced pressure to give the title compound (40.0 g, 87%) as a colourless oil; MS(ES+) m/e 230/232 $[M+H]^+$.

Step 2. 1-(4-Chloro-3-methoxy-phenyl)-2-pyridin-4-yl-ethanone

4-Picoline (16.9 ml, 0.174 mol) was added dropwise to a stirred solution of lithium di-isopropylamide (110 ml, 0.22 mol, 2M solution in heptane, ethylbenzene, tetrahydrofuran) in dry tetrahydrofuran (150 ml) at −78° C. After stirring at −78° C. for 15 minutes a solution of the product of Step 1 (40.0 g, 0.174 mol) in tetrahydrofuran (100 ml) was added dropwise. The reaction was allowed to warm to room temperature over 3 hours. The solution was cooled in ice and saturated ammonium chloride solution was added. The aqueous mixture was extracted with ethyl acetate, washed with brine, dried ($MgSO_4$), filtered and concentrated at reduced pressure. The resulting gum was triturated with cold diethyl ether/hexane (1:1, 300 ml) and the solid collected to give the title compound, as a pale yellow solid (29 g, 64%); MS(ES+) m/e 262/264 $[M+H]^+$.

Step 3. 1-(4-Chloro-3-methoxy-phenyl)-2-pyridin-4-yl)-ethane-1,2-dione

A solution of the product of Step 2 (22.5 g, 86 mmol) in dimethylsulphoxide (150 ml) was stirred at 55° C. Hydrogen bromide (48% aqueous, 21 ml) was added dropwise and the solution maintained at 55° C. for 1 hour. After cooling to room temperature, the solution was poured into a solution of sodium acetate (21 g) in ice-water (1 litre) and the resulting slurry was stirred at room temperature for 30 minutes. The mixture was extracted with ethyl acetate and the organic layers were combined, washed with brine, dried ($MgSO_4$), filtered and concentrated at reduced pressure. The residue was triturated with diethyl ether/hexane (1:4) and the solid collected to give the title compound as a yellow solid; MS(EI) m/e 275/277 $[M]^+$.

Step 4. 2-[4-(4-Chloro-3-methoxyphenyl)-5-pyridin-4-yl-1H-imidazol-2-yl]-2-methyl propionic acid methyl ester The product of Step 3 (11.03 g, 40 mmol), 2,2-dimethyl-3-oxo-propionic acid methyl ester (6.77 g, 52 mmol) and ammonium acetate (30.8 g, 400 mmol) were heated at 100° C. in acetic acid (100 ml) for 1 hour. The solution was concentrated under reduced pressure and the residue poured on to ice:0.880 ammonia solution. The solution was extracted with ethyl acetate, washed with water and brine, dried ($MgSO_4$) and evaporated to a solid. The solid was triturated with hexane, filtered and dried to afford the title compound (11.02 g, 71%) as a tan solid; MS(AP+) m/e 386/388$[M+H]^+$.

Description 2: 2-[4-(4-Chloro-3-methoxyphenyl)-5-pyridin-4-yl-1H-imidazole-2-yl]-2-methyl-propionic acid The product of D1 (11.03 g, 28 mmol) was suspended in methanol (150 ml), 2M sodium hydroxide solution (42 ml, 84 mmol) added and the mixture warmed to 50° C. for 3 hours. After concentration at reduced pressure, the residue was dissolved in water, washed with ethyl acetate and then acidified to pH 4-5 with acetic acid. The resulting white precipitate was filtered, washed with water and dried over phosphorous pentoxide at reduced pressure to afford the title compound (7.75 g, 74%) as a lemon solid; MS(AP+) m/e 372/374 $[M+H]^+$.

Description 3: 2-[4-(3,4-Dichlorophenyl)-5-pryidin-4-yl-1H-imidazole-2-yl]-2-methyl-propionic acid Step 1. 1-(3,4-Dichlorophenyl)-2-pyridin-4-yl-ethane-1,2-diol 4-(tert-Butyldimethylsilyloxymethyl)-pyridine (T. F. Gallagher et al, *Bioorganic and Medicinal Chemistry;* 1997, 5, 49) (67 g, 0.3 mol) was dissolved in THF (250 ml) and cooled to −40° C. The solution was treated with a 2M solution of lithuim diusopropylamide in THF (200 ml, 0.4 mol) and stirred for 45 minutes maintaining a temperature of −40 to −20° C., before the dropwise addition of 3,4-dichlorobenzaldehyde (55.13 g, 0.32 mol) in THF (250 ml). The mixture was allowed to warm to room temperature then stirred for a further 18 hours. After re-cooling to 0° C. the reaction was quenched with saturated ammonium chloride solution (500 ml), and the resulting two phase mixture separated. The aqueous phase was extracted with ethyl acetate and the combined organics concentrated under reduced pressure. The residue was dissolved in ethyl acetate, washed with saturated sodium bicarbonate solution, water and brine, dried ($MgSO_4$) and concentrated under reduced pressure to an oil (129 g). The oil was dissolved in THF (300 ml) and a 1M solution of tetrabutylammonium fluoride (360 ml, 0.36 mol) added dropwise. The solution was stirred at room temperature for 45 minutes, then concentrated to an oil under reduced pressure. The oil was dissolved in ethyl acetate and washed with saturated sodium bicarbonate solution, water and brine, dried ($MgSO_4$) and evaporated under reduced pressure. The oil was triturated with hexane and the resulting solid filtered and washed with hexane to afford the title compound (67.58 g 79%) as a tan solid; MS(AP+) m/e 284/286/288 $[M+H]^+$.

Step 2. 1-(3,4-Dichlorophenyl)-2-pyridin-4-yl-ethane-1,2-dione

Dimethylsulfoxide (37 ml, 0.53 mol) was dissolved in dichloromethane (250 ml) and cooled to −78° C. Oxalyl chloride (34.5 ml, 0.40 mol) was added dropwise and the solution stirred for 20 min. A solution of the product of Step 1 (34 g, 0.12 mol) in dimethylsulfoxide (40 ml) and dichloromethane (200 ml) was added dropwise at −78° C., and the solution stirred for 30 minutes. Triethylamine (104 ml, 0.74 mol) was added dropwise and the solution became floculent such that overhead stirring became necessary. The solution was allowed to stir at room temperature over 2 hours then was poured on to ice/saturated sodium bicarbonate solution. The aqueous layer was separated, and re-extracted with dichloromethane. The combined organic phases were concentrated under reduced pressure to a green-yellow solid. The solid was redissolved in dichloromethane and washed with water and brine, dried ($MgSO_4$) and evaporated to a solid. The crude solid was purified by silica gel chromatography eluting with dichloromethane, to afford the title compound (28.66 g, 85%) as a yellow solid; MS(-ve ion) m/e 279/281/283 $[M−H]^-$.

Step 3. 2-[4-(3,4-Dichlorophenyl)-5-pyridin-4-yl-1H-imidazol-2-yl]-2-methyl propionic acid methyl ester The product of Step 2 (5.60 g, 20 mmol) was reacted with 2,2-dimethyl-3-oxo-propionic acid methyl ester (3.38 g, 26 mmol) and ammonium acetate (15.4 g, 200 mmol) as described in Description 1, Step 4 to afford the title compound (5.06 g, 65%) as a tan solid; MS(AP+) m/e 391/393/395 [M+H]$^+$.

Step 4. 2-[4-(3,4-Dichlorophenyl)-5-pryidin-4-yl-1H-imidazole-2-yl]-2-methyl-propionic acid The product of Step 3 (5.26 g, 14 mmol) was reacted with 2M sodium hydroxide solution (20 ml, 40 mmol) in methanol as described in Description 2, to afford the title compound (2.36 g, 45%) as a beige solid; MS(AP+) m/e 376/378/380 [M+H]$^+$.

EXAMPLE 1 n-Butyl-2-[4-(4-chloro-3-methoxyphenyl)-5-pyridin-4-yl-1H-imidazole-2-yl] isobutylamide 1-(3-Dimethylaminopropyl)-3-ethylcarbodiimide hydrochloride (63 mg, 0.33 mmol) and 1-hydroxybenzotriazole hydrate (41 mg, 0.3 mmol) were added to a suspension of the product of Description 2 (111 mg, 0.3 mmol) in dichloromethane (5 ml). The mixture was stirred at room temperature until a clear yellow solution was obtained then n-butylamine (0.022 ml, 0.3 mmol) added. The solution was stirred at room temperature overnight then evaporated under reduced pressure to a solid. The solid was dissolved in ethyl acetate, washed with saturated sodium bicarbonate solution, water and brine, dried (MgSO$_4$) and evaporated under reduced pressure to afford the title compound (113 mg, 88%) as a cream solid; MS(AP-) m/e 425/427 [M-H]$^-$.

EXAMPLE 2 n-Butyl-2-[4-(4-chloro-3-hydroxyphenyl)-5-pyridin-4-yl-1H-imidazole-2-yl]isobutylamide The product of Example 1 (130 mg, 0.3 mmol) was dissolved in dichloromethane (5 ml) cooled to 0° C., then treated dropwise with 1M solution of boron tribromide in dichloromethane (1.2 ml, 1.2 mmol). After stirring at room temperature for 18 hours, the heterogeneous mixture was diluted with dichloromethane (10 ml), 2M hydrochloric acid (1 ml) added and the mixture heated at reflux for 30 min. After cooling to room temperature, the solution was basified with saturated sodium bicarbonate solution and extracted with dichloromethane. The combined organic extracts were washed with water and brine, dried (MgSO$_4$) and evaporated under reduced pressure to afford the title compound (101 mg, 82%) as yellow powder; MS(AP-) m/e 411/413 [M-H]$^-$.

EXAMPLE 3

2-[4-(3,4-Dichlorophenyl)-5-pyridin-4-yl-1H-imidazol-2-yl]-2-methyl-1-morpholin-4-yl-propan-1-one The product of Description 3 (113 mg, 0.3 mmol) was reacted with morpholine (0.027 ml, 0.3 mmol) as described in Example 1 to afford the title compound (66 mg, 49%) as a cream solid; MS(AP+) mr/e 445/447/449 [M+H]$^+$.

The following examples were prepared from the product of Description 2 by the general method described in Example 1.

| | Example | Amine | Characterisation |
|---|---|---|---|
| 4 | 2-[4-(4-Chloro-3-methoxy-phenyl)-5-pyridin-4-yl-1H-imidazol-2-yl]-2-methyl-1-pyrrolidin-1-yl-propan-1-one | Pyrrolidine | MS(AP+) m/e 426/428 [M + H]$^+$ |
| 5 | 2-[4-(4-Chloro-3-methoxy-phenyl)-5-pyridin-4-yl-1H-imidazol-2-yl]-N-(tetrahydro-furan-2-ylmethyl)-isobutyramide | Tetrahydro furfurylamine | MS(AP+) m/e 455/457 [M + H]$^+$ |
| 6 | 2-[4-(4-Chloro-3-methoxy-phenyl)-5-pyridin-4-yl-1H-imidazol-2-yl]-2-methyl-1-(4-methyl-piperazin-1-yl)-propan-1-one | N-methyl-piperazine | MS(AP+) m/e 454/456 [M + H]$^+$ |
| 7 | N-(2-Acetylamino-ethyl)-2-[4-(4-chloro-3-methoxy-phenyl)-5-pyridin-4-yl-1H-imidazol-2-yl]-isobutyramide | N-acetyl ethylene diamine | MS(AP+) m/e 455/457 [M + H]$^+$ |
| 8 | 2-[4-(4-Chloro-3-methoxy-phenyl)-5-pyridin-4-yl-1H-imidazol-2-yl]-N-pyridin-3-ylmethyl-isobutyramide | 3-(Aminomethyl) pyridine | MS(AP+) m/e 462/464 [M + H]$^+$ |
| 9 | 2-[4-(4-Chloro-3-methoxy-phenyl)-5-pyridin-4-yl-1H-imidazol-2-yl]-N-cyclopropyl-isobutyramide | Cyclopropylamine | MS(AP+) m/e 411/413 [M + H]$^+$ |
| 10 | 2-[4-(4-Chloro-3-methoxy-phenyl)-5-pyridin-4-yl-1H-imidazol-2-yl]-N-(2-methoxy-ethyl)-isobutyramide | 2-Methoxy ethylamine | MS(AP+) m/e 429/431 [M + H]$^+$ |

The following examples were prepared by the general method described in Example 2.

| Example | | Precursor | Characterisation |
|---|---|---|---|
| 11 | 2-[4-(4-Chloro-3-hydroxy-phenyl)-5-pyridin-4-yl-1H-imidazol-2-yl]-2-methyl-1-pyrrolidin-1-yl-propan-1-one | Example 4 | MS(AP+) m/e 412/414 [M + H]$^+$ |
| 12 | 2-[4-(4-Chloro-3-hydroxy-phenyl)-5-pyridin-4-yl-1H-imidazol-2-yl]-N-(tetrahydro-furan-2-ylmethyl)-isobutyramide | Example 5 | MS(AP+) m/e 441/443 [M + H]$^+$ |
| 13 | 2-[4-(4-Chloro-3-hydroxy-phenyl)-5-pyridin-4-yl-1H-imidazol-2-yl]-2-methyl-1-(4-methyl-piperazin-1-yl)-propan-1-one | Example 6 | MS(AP+) m/e 440/442 [M + H]$^+$ |
| 14 | N-(2-Acetylamino-ethyl)-2-[4-(4-chloro-3-hydroxy-phenyl)-5-pyridin-4-yl-1H-imidazol-2-yl]-isobutyramide | Example 7 | MS(AP+) m/e 441/443 [M + H]$^+$ |
| 15 | 2-[4-(4-Chloro-3-hydroxy-phenyl)-5-pyridin-4-yl-1H-imidazol-2-yl]-N-pyridin-3-ylmethyl-isobutyramide | Example 8 | MS(AP+) m/e 448/450 [M + H]$^+$ |
| 16 | 2-[4-(4-Chloro-3-hydroxy-phenyl)-5-pyridin-4-yl-1H-imidazol-2-yl]-N-cyclopropyl-isobutyramide | Example 9 | MS(AP+) m/e 397/399 [M + H]$^+$ |
| 17 | 2-[4-(4-Chloro-3-hydroxy-phenyl)-5-pyridin-4-yl-1H-imidazol-2-yl]-N-(2-methoxy-ethyl)-isobutyramide | Example 10 | MS(AP+) m/e 415/417 [M + H]$^+$ |

It is to be understood that the present invention covers all combinations of particular and preferred sub groups described hereinabove.

BIOLOGICAL EXAMPLES

The activity of compounds of formula (I) as B-Raf inhibitors may be determined by the following in vitro assay:

Raf Kinase Assay

Activity of human recombinant B-Raf protein was assessed in vitro by assay of the incorporation of radiolabelled phosphate to recombinant MAP kinase (MEK), a known physiologic substrate of B-Raf. Catalytically active human recombinant B-Raf protein was obtained by purification from sf9 insect cells infected with a human B-Raf recombinant baculovirus expression vector. To ensure that all substrate phosphorylation resulted from B-Raf activity, a catalytically inactive form of MEK was utilised. This protein was purified from bacterial cells expression mutant inactive MEK as a fusion protein with glutathione-S-transferase (GST-kdMEK).

Method: Standard assay conditions of B-Raf catalytic activity utilised 3 ug of GST-kdMEK, 10 uM ATP and 2uCi $^{33}$P-ATP, 50 mM MOPS, 0.1 mM EDTA, 0.1M sucrose, 10 mM MgCl$_2$ plus 0.1% dimethylsulphoxide (containing compound where appropriate) in a total reaction volume of 30 ul. Reactions were incubated at 25° C. for 90 minutes and reactions terminated by addition of EDTA to a final concentration of 50 uM. 10 ul of reaction was spotted to P30 phosphocellulose paper and air dried. Following four washes in ice cold 10% trichloroacetic acid, 0.5% phosphoric acid, papers were air dried prior to addition of liquid scintillant and measurement of radioactvity in a scintillation counter.

Results: The compounds of the examples were found to be effective in inhibiting B-Raf mediated phosphorylation of GST-kdMEK substrate having IC$_{50}$'s of <3 μM.

The activity of compounds as Raf inhibitors may also be determined by the assays described in WO 99/10325; McDonald, O. B., Chen, W. J., Ellis, B., Hoffman, C., Overton, L., Rink, M., Smith, A., Marshall, C. J. and Wood, E. R. (1999) A scintillation proximity assay for the Raf/MEK/ERK kinase cascade: high throughput screening and identification of selective enzyme inhibitors, Anal. Biochem. 268: 318-329 and AACR meeting New Orleans 1998 Poster 3793.

The neuroprotective properties of B-Raf inhibitors may be determined by the following in vitro assay:

Neuroprotective Properties of B-Raf Inhibitors in Rat Hippocampal Slice Cultures Organotypic cultures provide an intermediate between dissociated neuronal cell cultures and in-vivo models of oxygen and glucose deprivation (OGD). The majority of glial-neuronal interactions and neuronal circuitry are maintained in cultured hippocampal slices, so facilitating investigation of the patterns of death among differing cell types in a model that resembles the in vivo situation. These cultures allow the study of delayed cellular damage and death 24 hours, or more, post-insult and permit assessment of the consequences of long-term alterations in culture conditions. A number of laboratories have reported delayed neuronal damage in response to OGD in organotypic cultures of the hippocampus (Vornov et al., Stroke, 1994, 25, 57-465; Newell et al., Brain Res., 1995, 676, 38-44). Several classes of compounds have been shown to protect in this model, including EAA antagonists (Strasser et al., Brain Res., 1995, 687, 167-174), Na channel blockers (Tasker et al., J. Neurosci., 1992, 12, 98-4308) and Ca channel blockers (Pringle et al., Stroke, 1996, 7, 2124-2130). To date, relatively little is known of the roles of intracellular kinase mediated signalling pathways in neuronal cell death in this model.

Method: Organotypic hippocampal slice cultures were prepared using the method of Stoppini et al., J. Neurosci. Methods, 1995, 37, 173-182. Briefly, 400 micron sections prepared from hippocampi of 7-8 day postnatal Sprague Dawley rats are cultured on semiporous membranes for 9-12 days. OGD is then induced by incubation in serum and glucose-free medium in an anaerobic chamber for 45 minutes. Cultures are then returned to the air/CO$_2$ incubator for 23 hours before analysis. Propidium iodide (PI) is used as an indicator of cell death. PI is non toxic to neurones and has been used in many studies to ascertain cell viability. In damaged neurons PI enters and binds to nucleic acids. Bound PI shows increased emission at 635 nm when excited at 540 nm. One PI fluorescence image and one white light image are taken and the proportion of cell death analysed. The area of region CA1 is defined from the white light image and superimposed over the PI image. The PI signal is thresholded and area of PI damage expressed as a percentage of the CA1 area. Correlation between PI fluorescence and histologically confirmed cell death has been validated previously by Nissl-staining using cresyl fast violet (Newell et al., *J. Neurosci.*, 1995, 15, 7702-7711).

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

What is claimed is:

1. A compound of formula (I):

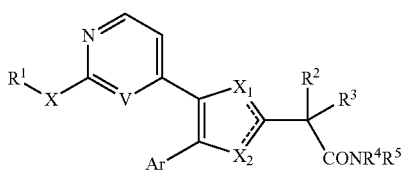

(I)

wherein

X is O, $CH_2$, S or NH, or the moiety X—R' is hydrogen;

V is CH or N;

$R^1$ is hydrogen, $C_{1-6}$alkyl, $C_{3-7}$cycloalkyl, aryl, aryl $C_{1-6}$alkyl, heterocyclyl, heterocyclyl$C_{1-6}$alkyl, heteroaryl, or heteroaryl$C_{1-6}$alkyl any of which except for hydrogen are optionally substituted;

$R^2$ and $R^3$ independently represent optionally substituted $C_{1-6}$alkyl, or $R^2$ and $R^3$ together with the carbon atom to which they are attached form an optionally substituted $C_{3-7}$cycloalkyl or $C_{3-7}$cycloalkenyl ring, or $R^2$ and $R^3$ together with the carbon atom to which they are attached form an optionally substituted 5 to 7-membered heterocyclyl ring containing up to 3 heteroatoms selected from N, O, and S;

$R^4$ and $R^5$ independently represent hydrogen, $C_{1-6}$alkyl, $C_{3-7}$cycloalkyl, aryl, aryl$C_{1-6}$alkyl, heteroaryl, heteroaryl$C_{1-6}$alkyl, heterocyclyl, or heterocyclyl $C_{1-6}$alkyl, any of which, except for hydrogen, may be optionally substituted, or $R^4$ and $R^5$ together with the nitrogen atom to which they are attached form 4- to 8-membered ring;

Ar is an aryl or heteroaryl ring either of which are optionally substituted;

one of $X_1$ and $X_2$ is N and the other is $NR^6$, wherein $R^6$ is hydrogen, $C_{1-6}$alkyl, or aryl$C_{1-6}$alkyl;

or a pharmaceutically acceptable salt thereof, wherein:

alkyl groups, $C_{3-7}$cycloalkyl rings and $C_{3-7}$cycloalkenyl rings are optionally substituted with one or more groups selected from the group consisting of aryl, heteroaryl, heterocyclyl, $C_{1-6}$alkoxy, $C_{1-6}$alkylthio, aryl$C_{1-6}$alkoxy, aryl$C_{1-6}$alkylthio, amino, mono- or di-$C_{1-6}$alkylamino, cycloalkyl, cycloalkenyl, carboxy and esters thereof, amide, sulphonamido, ureido, guanidino, $C_{1-6}$alkylguanidino, amidino, $C_{1-6}$alkylamidino, $C_{1-6}$acyloxy, azido, hydroxy, hydroxyimino and halogen; and aryl, heterocyclyl and heteroaryl rings are optionally substituted with one to three substituents selected from the group consisting of halogen, $C_{1-6}$alkyl, aryl, aryl $C_{1-6}$alkyl, $C_{1-6}$alkoxy, $C_{1-6}$alkoxy $C_{1-6}$alkyl, halo $C_{1-6}$alkyl, aryl$C_{1-6}$alkoxy, hydroxy, nitro, cyano, azido, amino, mono- and di-N-$C_{1-6}$alkylamino, acylamino, arylcarbonylamino, acyloxy, carboxy, carboxy salts, carboxy esters, carbamoyl, mono- and di-N-$C_{1-6}$alkylcarbamoyl, $C_{1-6}$alkoxycarbonyl, aryloxycarbonyl, ureido, guanidino, $C_{1-6}$alkylguanidino, amidino, $C_{1-6}$alkylamidino, sulphonylamino, aminosulphonyl, $C_{1-6}$alkylthio, $C_{1-6}$alkylsulphinyl, $C_{1-6}$alkylsulphonyl, heterocyclyl, heteroaryl, heterocyclyl $C_{1-6}$alkyl, hydroxyimino-$C_{1-6}$alkyl and heteroaryl $C_{1-6}$alkyl.

2. A compound according to claim 1 wherein X—$R^1$ is hydrogen.

3. A compound according to claim 1 wherein Ar is phenyl.

4. A compound according to claim 3 wherein Ar is substituted by up to 3 substituents independently selected from halo, hydroxy, hydroxy $C_{1-6}$alkyl, hydroxyimino $C_{1-6}$alkyl, and $C_{1-6}$alkoxy.

5. A compound as claimed in claim 1 wherein $R^2$ and $R^3$ represent $C_{1-6}$alkyl, or $R^2$ and $R^3$ together with the carbon atom to which they are attached form an optionally substituted $C_{3-7}$cycloalkyl ring.

6. A compound as claimed in claim 1 wherein $R^4$ and $R^5$ are independently hydrogen, $C_{1-6}$alkyl, aryl$C_{1-6}$alkyl, $C_{3-7}$cycloalkyl any of which except hydrogen are optionally substituted, or $R^4$ and $R^5$ together with the nitrogen to which they are attached form an optionally substituted 5 or 6 membered ring optionally containing up to 2 heteroatoms selected from N or O.

7. A compound selected from the group consisting of:

n-Butyl-2-[4-(4-chloro-3-methoxphenlyl)-5-pyridin-4-yl-1H-imidazole-2-yl]isobutylamide;

n-Butyl-2-[4-(4-chloro-3-hydroxyphenyl)-5-pyridin-4-yl-1H-imidazole-2-yi]isobutylamide;

2-[4-(3,4-Dichlorophenyl)-5-pyridin-4-yl-1H-imidazol-2-yl]-2-methyl-1-morpholin-4-yl-propan-1-one;

2-[4-(4-Chloro-3-methoxy-phenyl)-5-pyridin-4-yl-1H-imidazol-2-yl]-2-methyl-1-pyrrolidin-1-yl-propan-1-one;

2-[4-(4-Chloro-3-methoxy-phenyl)-5-pyridin-4-yl-1H-imidazol-2-yl]-N-(tetrahydro-furan-2-ylmethyl)-isobutyramide;

2-[4-(4-Chloro-3-methoxy-phenyl)-5-pyridin-4-yl-1H-imidazol-2-yl]-2-methyl-1-(4-methyl-piperazin-1-yl)-propan-1-one;

N-(2-Acetylamino-ethyl)-2-[4-(4-chloro-3-methoxy-phenyl)-5-pyridin-4-yl-1H-imidazol-2-yl]-isobutyramide;

2-[4-(4-Chloro-3-methoxy-phenyl)-5-pyridin-4-yl-1H-imidazol-2-yl]-N-pyridin-3-ylmethyl-isobutyramide;

2-[4-(4-Chloro-3-methoxy-phenyl)-5-pyridin-4-yl-1H-imidazol-2-yl]-N-cyclopropyl-isobutyramide;

2-[4-(4-Chloro-3-methoxy-phenyl)-5-pyridin-4-yl-1H-imidazol-2-yl]-N-cyclopropyl-isobutyramide;

2-[4-(4-Chloro-3-hydroxy-phenyl)-5-pyridin-4-yl-1H-imidazol-2-yl]-2-methyl-1-pyrrolidin-1-propan-1-one;

2-[4-(4-Chloro-3-hydroxy-phenyl)-5-pyridin-4-yl-1H-imidazol-2-yl]-N-(tetrahydro-furan-2-ylmethyl)-isobutyramide;

2-[4-(4-Chloro-3-hydroxy-phenyl)-5-pyridin-4-yl-1H-imidazol-2-yl]-2-methyl-1-(4-methyl-piperazin-1-yl)-propan-1-one;

N-(2-Acetylamino-ethyl)-2-[4-(4-chloro-3-hydroxy-phenyl)-5-pyridin-4-yl-1H-imidazol-2-yl]-isobutyramide;

2-[4-(4-Chloro-3-hydroxy-phenyl)-5-pyridin-4-yl-1H-imidazol-2-yl]-N-pyridin-3-ylmethyl-isobutyramide;

2-[4-(4-Chloro-3-hydroxy-phenyl)-5-pyridin-4-yl-1H-imidazol-2-yl]-N-cyclopropyl-isobutyramide; and 2-[4-(4-Chloro-3-hydroxy-phenyl)-5-pyridin-4-yl-1H-imidazol-2-yl]-N-(2-methoxy-ethyl)-isobutyramide.

8. A pharmaceutical composition comprising a compound according to claim 1 or a pharmaceutically acceptable salt thereof and a pharmaceutically acceptable carrier.

9. A compound of formula (II):

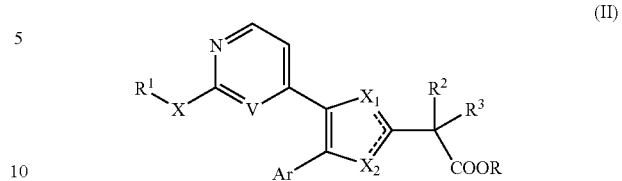

(II)

wherein X, V, $R^1$, $R^2$, $R^3$, Ar, $X_1$ and $X_2$ are as defined for formula (I) and R is hydrogen or aryl$C_{1-6}$alkyl.

* * * * *